United States Patent [19]

Anderson

[11] Patent Number: 5,364,389
[45] Date of Patent: Nov. 15, 1994

[54] METHOD AND APPARATUS FOR SEALING AND/OR GRASPING LUMINAL TISSUE

[75] Inventor: Dallas W. Anderson, The Woodlands, Tex.

[73] Assignee: Premier Laser Systems, Inc., Irvine, Calif.

[21] Appl. No.: 981,197

[22] Filed: Nov. 25, 1992

[51] Int. Cl.⁵ .......................................... A61B 17/36
[52] U.S. Cl. ..................................... 606/8; 606/27; 606/153; 606/15
[58] Field of Search .................. 606/8, 27, 40, 153, 606/154, 215, 15, 16, 17, 7

[56] References Cited

U.S. PATENT DOCUMENTS

| | | | |
|---|---|---|---|
| 4,633,870 | 1/1987 | Sauer | 606/8 |
| 4,892,098 | 1/1990 | Sauer | 606/8 |
| 4,907,591 | 3/1990 | Vasconcellos et al. | 606/154 |
| 5,026,367 | 6/1991 | Leckrone et al. | 606/7 |
| 5,061,265 | 10/1991 | Abela et al. | 606/7 |

FOREIGN PATENT DOCUMENTS 0480293  4/1992  European Pat. Off. ............ 606/153

Primary Examiner—Stephen C. Pellegrino
Assistant Examiner—Sonya C. Harris
Attorney, Agent, or Firm—Steven C. Stewart; James H. Beusse

[57] ABSTRACT

A method and apparatus for sealing and/or grasping lesions or incisions of luminal tissue is provided. The apparatus has a generally tubular assembly with portions which expand away from each other. The apparatus is inserted into the lumen of a tissue and placed adjacent the area to be sealed. The portions expand to contact the inner wall of the luminal tissue. Energy is delivered with a media through the expanded tubular assembly to heat the tissue to a nondestructive range where the tissue forms a denatured proteinaceous substance. The media delivering the energy is rotated in the expanded tubular assembly to heat different areas of the tissue without moving the tubular assembly itself. In an alternate embodiment of the invention, tubular portions of the assembly are provided which have side edges that slide toward and away from each other. The assembly is placed in the lumen and the tissue edges are inserted into the assembly between the side edge. The side edges then slide toward each other to hold the tissue edges in tight approximation while energy sufficient to form a denatured proteinaceous substance is applied to the tissue.

11 Claims, 5 Drawing Sheets

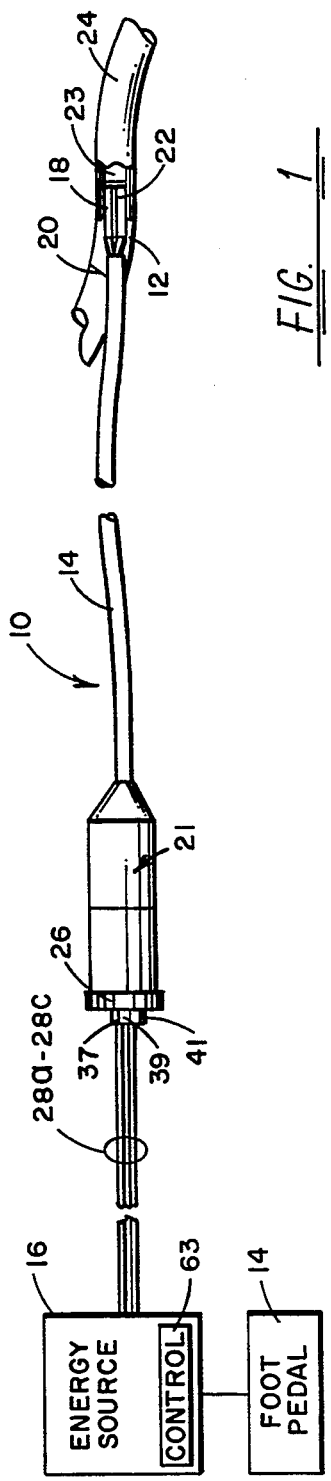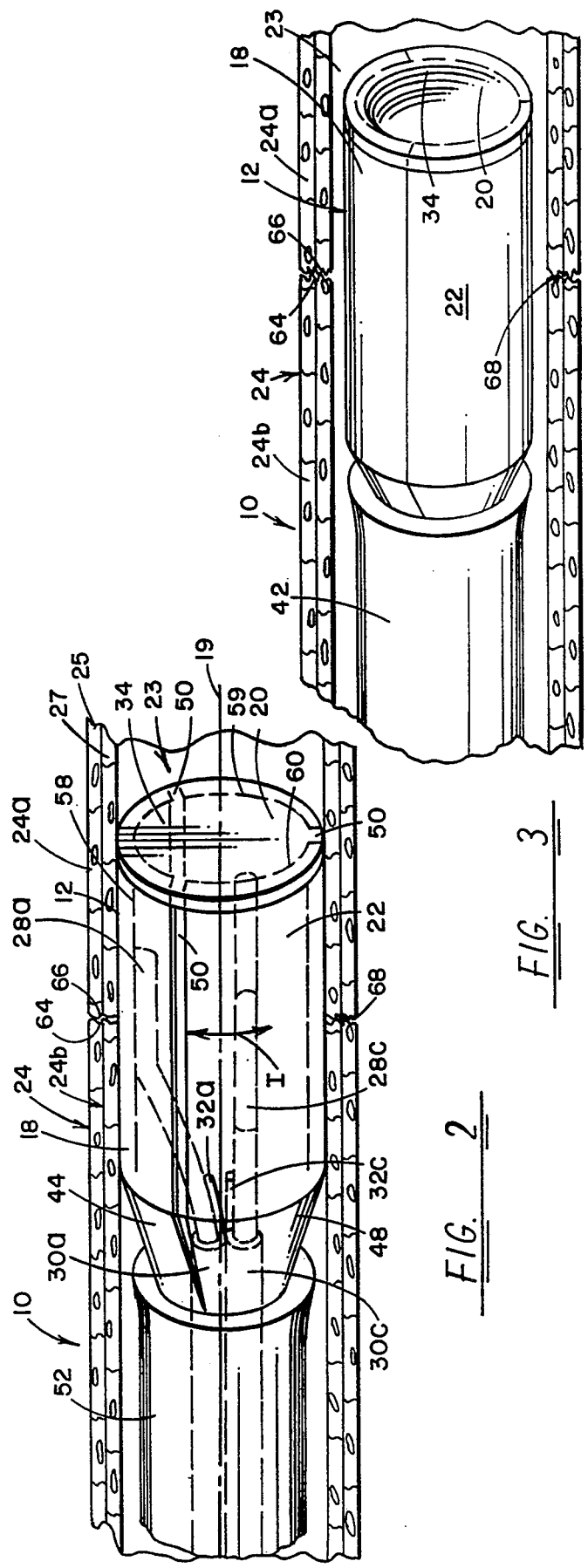

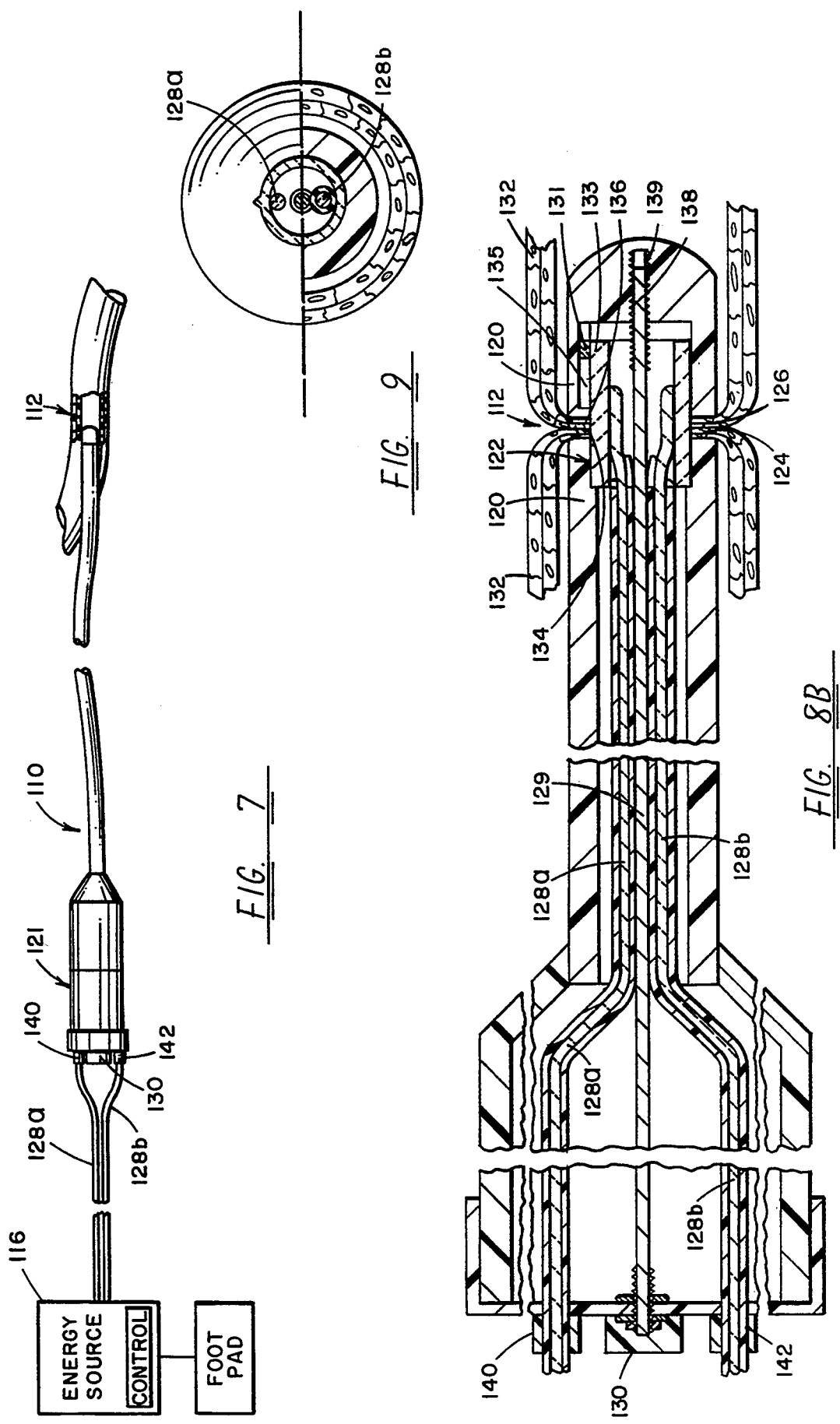

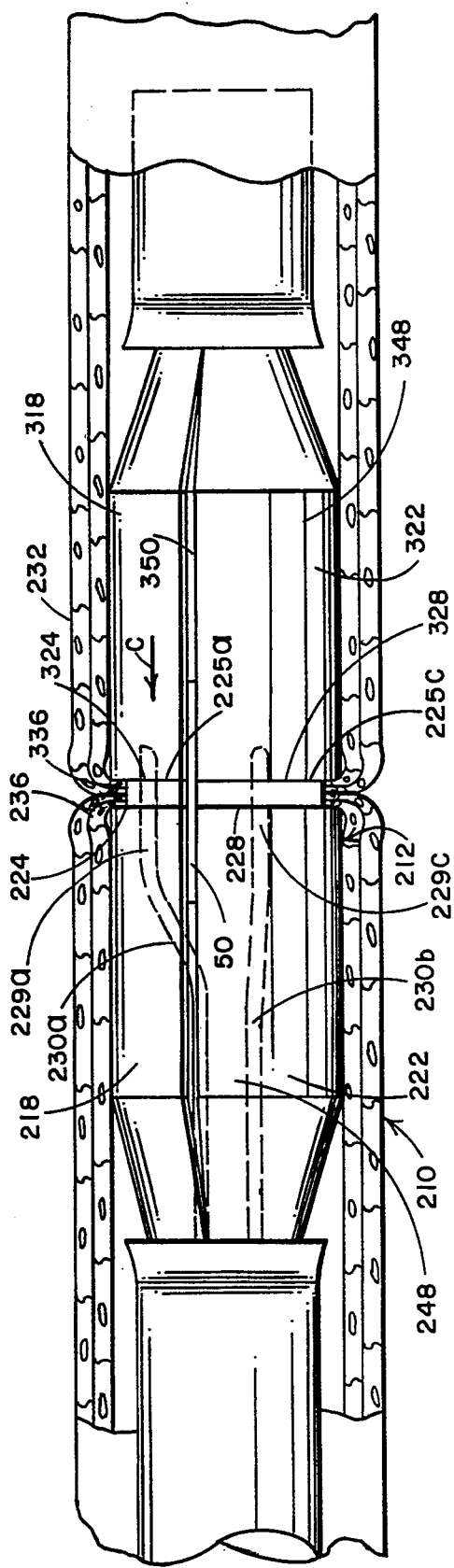
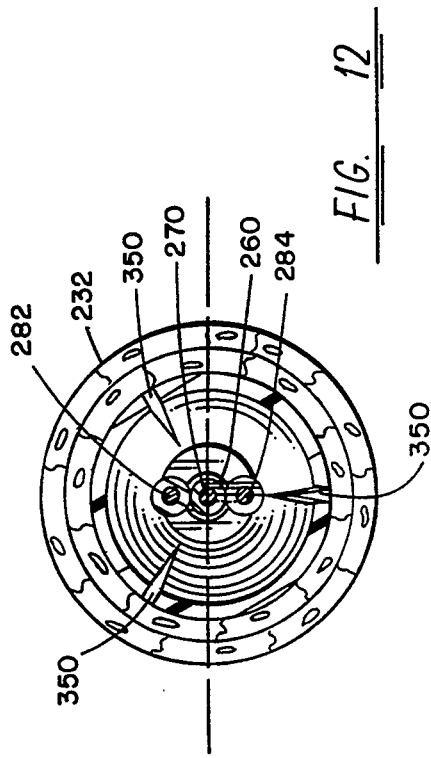

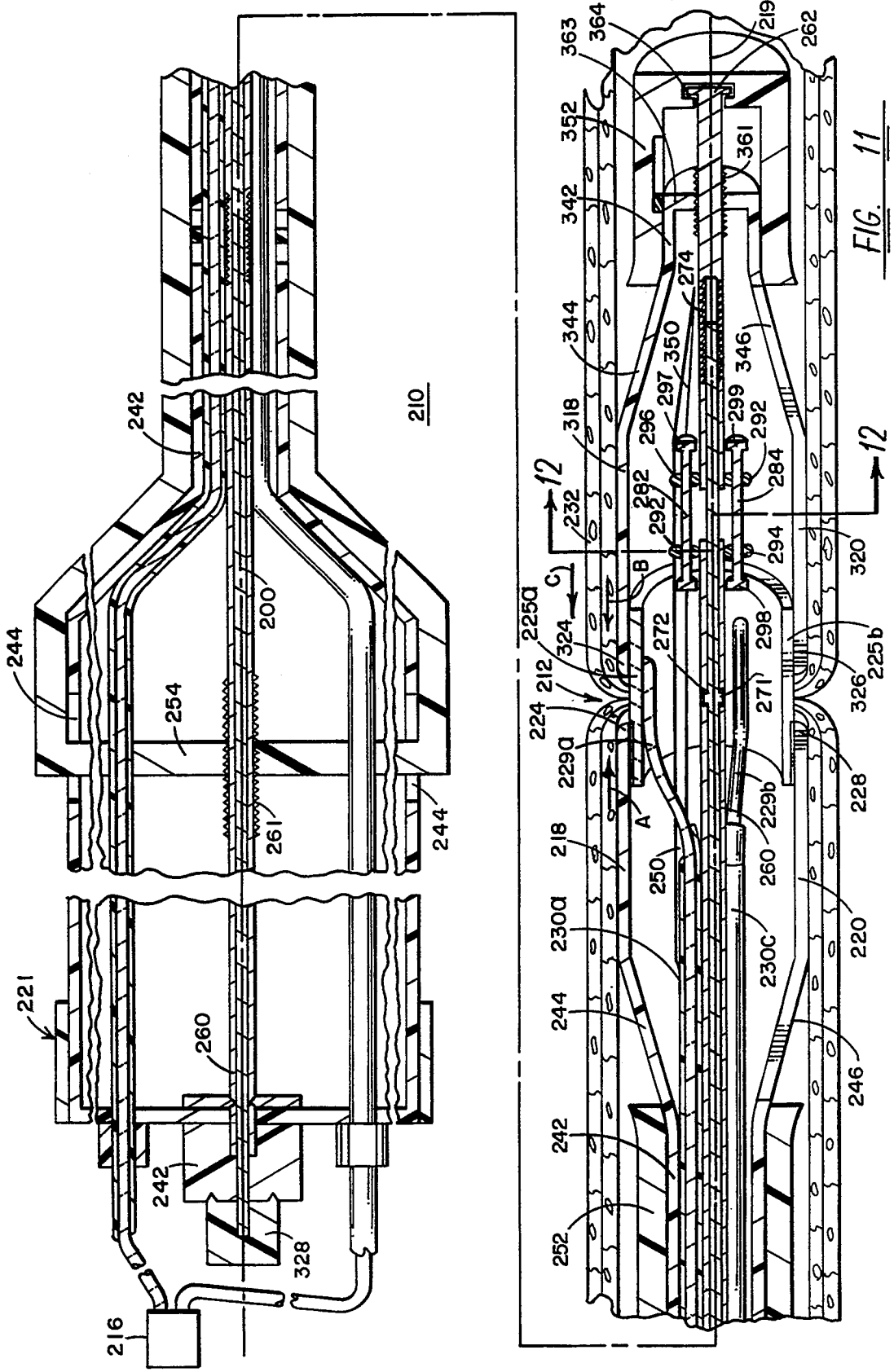

METHOD AND APPARATUS FOR SEALING AND/OR GRASPING LUMINAL TISSUE

BACKGROUND OF THE INVENTION

This invention relates to a method and apparatus for applying thermal energy to biological luminal tissue whereby tissue is converted to a denatured protein substance to join tightly approximated luminal tissue segments, and, more particularly to a method and apparatus for reconstructing severed luminal tissue, including vessels and ducts by use of a device which is inserted into the tissues lumen and directs thermal energy onto and through various areas on the tissue's inner walls to denature the protein substance therein.

Optical energy transformed to thermal energy has been used to convert biological tissue into a denatured proteinaceous substance for facilitating healing and wound closure. This healing technique is referred to generally as laser tissue welding. Examples of such laser tissue welding methods are described in U.S. Pat. Nos. 4,672,969, 4,854,320, 5,002,051, and 5,140,984. These methods deliver optical energy to tightly approximated tissue in the vicinity of a wound. This application of thermal energy results in the denaturation of tissue protein including collagen, with disruption of the cell walls which allows the intra- and intercellular fluids to mix, additional heat further denatures this protein soup which binds together creating something akin to a "biological glue".

In many prior methods of optical energy wound closure, thermal energy is delivered through an optical fiber to the tissue being reconstructed. Typically, one end of the fiber is connected to a laser that supplies optical energy to the wound site. Another end of the fiber is typically spaced a predetermined distance from the tissue, the distance depending on the tissue type. A foot pedal or hand held device activates and deactivates the laser. The parameters such as intensity and duration of the optical energy are controlled so that substantially all of the tissue being heated is raised to a predetermined non-destructive temperature range. The minimum predetermined non-destructive temperature is one at which tissue is converted to a denatured proteinaceous substance. The maximum predetermined non-destructive temperature is one at which water in the tissue boils.

Other methods known for healing and wound closure include suturing and stapling. These methods are used in endo-surgery or minimally invasive surgery in combination with various types of scopes, such as endoscopes, laparoscope, arthroscopes, etc. These scopes along with other medical equipment are inserted by a surgeon through incisions in the patient and then moved to the wound area being repaired. The scope is connected to a monitor so that the surgeon can view the procedure while the surgery is being performed.

Laser tissue welding may be used in minimally invasive and open surgery to repair vessels; however, conducting certain minimally invasive and open operations using laser welding surgery can be unnecessarily tedious as the surgeon welds at successive points along the circumference of the vessel or duct. This welding process is complicated because the distal end of the optical media that directs the energy for the welding must be placed a predetermined distance to the tissue being reconstructed or the area being reconstructed. If the distal end of the media is not at the predetermined distance from the area being sealed or reconstructed, the tissue temperature would be outside the aforementioned predetermined temperature range for proper tissue fusion.

Critical to current tissue welding methods is the necessity to place edges of tissue being repaired in tight approximation. Placing the tissue edges in close or tight proximity allows the denatured tissue constituents to form an intercellular matrix resulting in tissue fusion.

Certain luminal tissue types are very difficult for the surgeon to access with current thermal sealing techniques. Consequently, to thermally seal certain organs and vessels, the surgeon may have to cut or displace other organs that are in the way. This can create complications and can be time consuming.

Another sealing technique such as the one disclosed in U.S. Pat. No. 4,892,098, to Sauer requires that a stent device be placed within the lumen of the tissue being sealed for support at a wound. A circular housing is then placed around the tissue and fed optical energy to seal the wound. The proper placement of this stent device and the set up of the circular housing can be time consuming and result in an inconsistent application of optical energy.

One solution to overcoming inconsistent application of optical energy is disclosed in the apparatus described in U.S. patent application Ser. No. 07/963585, filed Oct. 20, 1992. This application discloses an apparatus containing one or more media elements. The apparatus is fed into the lumen adjacent to the area to be sealed. Energy sufficient to denature the tissue is delivered with the media elements (such as an optical fiber) through the apparatus to the inner walls of the lumen.

It is necessary to seal luminal tissue having highly elastic properties. In these instances, avoiding retraction and rotation of the tubular apparatus sealing the tissue allows the approximated tissue edges to maintain their position relative to each other. If it is necessary to grasp and hold the approximated elastic tissue edges, rotating the tubular apparatus would be problematical.

In some applications it is necessary to seal luminal tissue having a small outer diameter. In these instances only a limited amount of the media elements can be placed in the apparatus. Thus to seal more than one area around the perimeter of a luminal tissue, the apparatus must be rotated thereby decreasing sealing time and precision.

One procedure for sealing edges of some luminal tissues, such as a colon, involves placing an elongated tubular device that contains a circular cutting blade and a stapler inserted into the colon. Sides of the device clamp edges of the colon tissue together. The stapler then injects staples into the tissue edges to create a circumvential seal. The excess tissue around the circumference of the lumen is then cut with the blade. A drawback to this procedure are that staples left are in the tissue. Foreign bodies can later have adverse effect on the patient.

SUMMARY OF THE INVENTION

An object of this invention is to provide an improved method and apparatus for reconstructing luminal organs such as tissue, ducts, or vessels.

Another object of this invention is to provide an apparatus through which laser welding energy passes and is directed at the inner walls of luminal organs that are to be sealed, fused, or ligated.

It is also an object of this invention to place a device in the lumen of an organ to cause the formation of a proteinaceous framework of denatured protein in the vicinity of biological tissue to seal tissue, ducts, and vessels with greater efficiency and less time.

It is also an object of this invention to reconstruct transected vessels, organs, and ducts that have incisions by placing an apparatus into the lumen of the vessel and delivering energy to areas along the incision seam completely circumscribing the lumen while maintaining the integrity of the organ and lumen and without moving the apparatus.

It is further an object of this invention to reconstruct tissue with any energy source, such as an ultrasonic or thermal source, while maintaining at all times proper distance between a media delivering the energy to the tissue itself so that the final temperature of the tissue may be precisely maintained.

It is a further object of this invention to seal and pull together luminal tissue edges without leaving foreign bodies in the tissue.

These and other objects are accomplished with an apparatus for sealing luminal tissue having an inner wall. The apparatus includes a generally tubular assembly having a first portion and second portion. The first portion is operative to expand away from the second portion to engage the inner wall of the luminal tissue. A source of energy sufficient to heat tissue to form a denatured proteinaceous substance is connected to a delivering device that delivers energy from the source through at least one of the portions when the tubular portion expands to engage the tissue. The delivery device is operative to apply energy to heat an area on the tissue within a nondestructive range bounded by a minimum temperature at which tissue forms a denatured proteinaceous substance and a maximum temperature at which water in the tissue would boil. A internal mechanism which rotates the delivery device is placed within the tubular assembly to heat another area on the tissue within the nondestructive range without changing the orientation of the tubular assembly in the lumen. In this manner, the tissue can be sealed without having to retract and rotate the entire tubular portion.

In another embodiment of the invention, an apparatus for sealing an incision or lesion on a luminal tissue is provided. The apparatus has a first and second generally cylindrical outer portions each having an oppositely facing side edge. The cylindrical outer portions enclose a generally tubular inner portion having an outer wall. A device engages with the one of the cylindrical outer portions to slide the cylindrical outer portions on the tubular inner portion toward the other cylindrical outer portion to move one of the side edges toward the other of the side edges. When the side edges are drawn toward each other, the side edges urge the edges of the incision or lesion together in tight approximation and against the outer wall of the tubular inner portion. A source of energy sufficient to heat tissue to form a denatured proteinaceous substance is fed through a delivery device and the tubular inner portions at the tightly approximated edges of the tissue. The delivery means is operative to apply energy to heat an area on the tightly approximated tissue within a nondestructive range bounded by a minimum temperature at which tissue forms a denatured proteinaceous substance and a maximum temperature at which water in the tissue would boil. Preferably the first cylindrical outer portion has a first outer portion and second outer portion, and the first outer portion is operative to expand radially away from the second outer portion to engage the inner wall of the luminal tissue.

In another aspect of the invention a method for sealing edges of lesions or incisions on luminal tissue is disclosed. In the method oppositely facing side edges of a first and second generally cylindrical outer portion are aligned. The first and second generally cylindrical outer portion enclose a generally tubular inner portion having an outer wall. The first and second generally cylindrical outer portion and the enclosed inner portion are placed into the luminal tissue. The edges of the incision or lesion are placed between the oppositely facing side edges. At least one of the cylindrical outer portions is then slid on the tubular inner portion to draw one of the side edges toward the other of the side edges. Next the edges of the incision or lesion are urged together in tight approximation and against the outer wall of the tubular inner portion when the side edges are drawn toward each other. A source of energy is provided that heats tissue to form a denatured proteinaceous substance. The energy is delivered from the source with a delivery device which directs energy through the tubular inner portion at the tightly approximated edges of the tissue. Energy is applied to heat an area on the tightly approximated tissue within a nondestructive range bounded by a minimum temperature at which tissue forms a denatured proteinaceous substance and a maximum temperature at which water in the tissue would boil.

BRIEF DESCRIPTION OF THE DRAWINGS

FIG. 1 is a perspective view of one embodiment of the invention having an expansion assembly fed energy from an the energy source and that is inserted in the lumen of an organ;

FIG. 2 is a perspective view of the expansion assembly in FIG. 1 in an expanded position while inserted in the lumen of an organ;

FIG. 3 is a perspective view of the expansion assembly shown in FIG. 2 in a contracted position;

FIG. 4 is a side section view of the expansion assembly shown in FIG. 2;

FIG. 5 is a cross-section view of the expansion assembly along line 5—5 of FIG. 4;

FIG. 6 is a cross-section view of the expansion assembly along line 6—6 of FIG. 4;

FIG. 7 is a perspective view of another embodiment of the invention having a retraction assembly inserted into the lumen of an organ to seal edges of an incision or lesion;

FIG. 8A and 8B are cross-sectional views of the contraction assembly shown in FIG. 7, where FIG. 8A is the assembly in its expanded position and FIG. 8B is the assembly in its contracted position.

FIG. 9 is a cross-section view of the assembly shown in FIG. 8 along line 9—9;

FIG. 10 is a perspective view of another alternate embodiment of the invention for sealing luminal tissue which expands and contracts both forward and outward; and FIG. 11 is a side section view of the sealing apparatus shown in FIG. 10; and FIG. 12 is a cross-sectional view of the apparatus shown in FIG. 11 along line 12—12.

DESCRIPTION OF THE PREFERRED EMBODIMENTS

Figures 4, 5, 6, 8A:
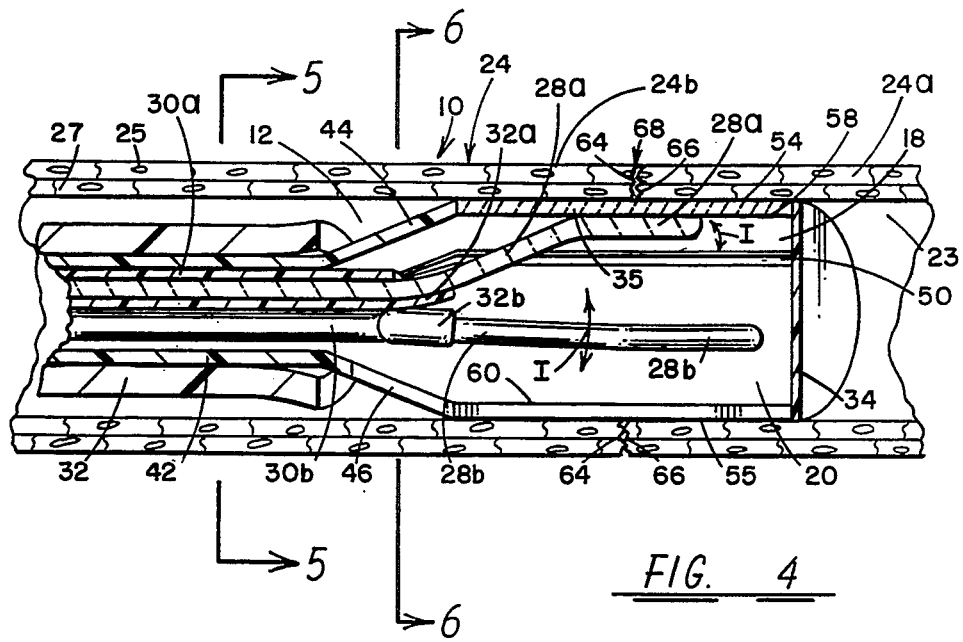

Referring to FIGS. 1-4, there is shown an apparatus 10 for sealing tissue in a lumen 23 of an organ 24. Apparatus 10 includes an expansion assembly 12 that is fed energy through conduit 14 from energy source 16 (FIG. 1). Assembly 12 includes a first portion 18, a second portion 20 and a third portion 22, which engage and disengage with the inner walls of luminal tissue or organ 24. Apparatus 10 has a handle assembly 21 which controls the position of assembly 12 in the organ 24. Portions 18-22 engage and disengage the inner walls of the organ 24 in response to handgrip 26 on assembly 21 being turned clockwise and counterclockwise by the user.

The preferred energy from source 16 is coherent light energy, although any energy source which heats tissue to form a denatured proteinaceous substance may be used including an ultrasonic energy source and a radiation energy source. For the purposes of example the invention will be described using a coherent light or optical energy source.

Optical energy from the energy source 16 is fed through conduit using media 28a-28c, such as a fiber optic cable having a proximate end distal end. The proximate end of media 28a-28c is optically connected to energy source 16. Media 28a-28c extends through rotatable tubes 30a-30c, respectively, in conduit 14. Referring to FIGS. 2 and 4, the distal end of fiber optic media 28a-28b exits tubes 38a-38c, respectively and terminates in assembly 12. Optical energy exits the distal end of fiber optic media 28a-28c and is directed at the inner walls of organ 24. Referring to FIGS. 2, 4 and 6, deflectors 32a-32c are mounted on the distal end of tubes 30a-30c, respectively, to rotate media 28a and 28b within assembly 12 to heat another area on organ 24 without changing the orientation of tubular expansion assembly 12 relative to organ 24.

Referring to FIGS. 2 and 4, depending on the application that apparatus 10 is being used, the manner media 28a-28c delivers the optical energy to the tissue can be through various ways, such as side firing (FIGS. 2 and 4), and end firing (not shown) or other known techniques. Preferably, portions 18-22 are constructed, or at least partially constructed, from a material 35 that is transmissive to the optical energy exiting media 28a-28c which heats organ 24. Examples of such material include plastics and quartz. The distal end of media 28a-28c may be positioned adjacent surfaces 58-62 of portions 18-22, respectively, may be embedded in surfaces 58-62, may direct optical energy through an aperture (not shown) in surfaces 58-62, or may directly contact organ 24.

Preferably, the distal ends of portions 18-22 are sealed with an elastic material 34 to prevent fluid in the lumen from entering assembly 12. This elastic material 34 would be flexible enough to permit portions 18-22 to expand and contract.

Referring to FIGS. 4-6, the lumen 23 of organ 24 is hollow and through which fluid flows. Surrounding lumen 23 is an outer layer of tissue 25 and an inner layer of tissue 27. The use of the words "tubular organs" throughout this application is meant to include all tissue containing a lumen, such as vessels, ducts and arteries. The use of the word "lumen" is defined as a cavity or the channel within any organ or structure of the body. Assembly 12 engages with outer layer 27 to seal lesions, closely approximated edges or an incision in a tubular organ.

Although not shown, assembly 12 may include one or more feedback sensors which detect changes in temperature of the organ. The feedback sensors could be used to convert detected optical energy to signals which would be fed to laser energy source 16. Optical energy source 16 then responds to the signals by adjusting the optical energy fed to the media 28a-28c to maintain the temperature of tissue being heated within a predetermined nondestructive temperature range. An optical viewing mechanism may be attached to the distal and/or proximal portions of the surfaces of portions 18-22 to help determine placement of the apparatus 12 in lumen 23.

The minimum temperature in the predetermined nondestructive temperature range is the temperature at which tissue is converted to a denatured proteinaceous substance. The maximum temperature in the predetermined non-destructive temperature range is the temperature at which water in the tissue boils.

Referring to FIG. 1, energy source 16 is activated in response to a foot pedal 40 or a trigger assembly (not shown) being activated. Preferably energy source 16 transmits coherent light energy in the frequency range of about 1.2-1.4 microns. Foot pedal 40 is depressed to enable optical energy source 16. The parameters of the energy from energy source 16 feeding optical energy through media 28a-28c is dependent on the thickness of tissue of the walls of organ 24 to be reconstructed. Examples of these parameters and preferable distances between the ends of fiber optic media 28a-28c and the surface of inner walls of organ 24 (i.e. the thickness of transmissive material 34) are summarized in the following Table I. These parameters are by no means all exclusive. It is envisioned that other parameters can be used with modifications and is intended that this table be exemplary of a preferred embodiment only.

TABLE I

| | LASER PARAMETERS FOR VARIOUS ORGAN TYPES | | | | | |
|---|---|---|---|---|---|---|
| Organ type | Organ Diameter (mm) | Predetermined Distance from media to Organ (with 400μ fiber) (mm) | Spot Size Diameter (mm) | Range of Power (Watts) | Exposure Duration On/Off | Approximate Final Energy Transferred to Organ (J/CM$^2$) |
| Fallopian Tube | 3 | 1 | .574-646 | .65-.85 | 0.5 sec/0.5 sec | 117-144 |
| Vas Deferens | 3 | 1 | .574-646 | .65-.85 | 0.5 sec/0.5 sec | 117-144 |

Referring to FIGS. 2-4, portions 18, 20 and 22 are shown connected to cylindrical throat portion 42 through tapered portions 44, 46 and 48, respectively. Portions 18-22 are separated by gap 50 and engage each other along one end of the gap 50. An elongated cylindrical section 52 encircles throat portion 42. A cable, or other conventional mechanism (not shown), connects handgrip 26 to throat portion 42 and cylindrical section 52. This mechanism responds to handgrip 26 being turned to force section 52 to slide along tapered portion 44, 46 and 48. Due to the elastic properties of the materials to which portions 18, 20 and 22 are constructed, tubular portions 18–22 expand away from and contract toward each other in an outwardly circular manner when section 52 slides back and forth along tapered portions 44, 46 and 48.

Referring to FIGS. 4 and 6, portions 18, 20 and 22 have respective outside surfaces 54, 55 and 56 and inner surfaces 58, 59 and 60 constructed with a layer of transmissive material 35 (FIG. 4) shaped of generally arcuate curvature. Portions 18, 20 and 22 expand radially outward away from an axis 19 (FIG. 2) extending longitudinally through assembly 12 to engage with the inner wall of organ 24. By transmissive material is intended to mean any material which is substantially transparent to the frequency of the optical energy being emitted at the distal end of media 28a–28c.

Referring to FIG. 2 and FIG. 4, the distal ends of media 28a–28c may be positioned at various locations adjacent the transmissive material 35 depending on the application and tissue type. For example, the distal ends of the media would be placed laterally along side each other if assembly 12 were used to seal lengthwise slits in an organ. If the assembly 12 were used to seal seams, the distal end of the media would be placed on opposing inner surfaces of portions 18, 20 and 22 as shown in FIGS. 2 and 4.

Referring to FIG. 2 and 4, the distal ends of media 28a–28c preferably terminates adjacent the inner surfaces 58, 60 and 62, respectively, of the transmissive material 35. The thickness of the transmissive material is selected to maintain a predetermined distance between the end of fiber optic media 28a–28c and the surface of the inner wall of organ 24. The predetermined distance is selected in accordance with the organ 24 type and thickness as detailed in Table I.

Referring to FIG. 1, energy source contains a control 63 that adjusts rate at which optical energy is applied to organ 24 to be within a nondestructive range by a minimum rate at which tissue forms a denatured proteinaceous substance and a maximum rate at which water in the tissue would boil. The rate as used herein is defined as the power and duration of the optical energy applied to the organ. An exemplary control device is described in U.S. Pat. No. 4,854,320 which is hereby incorporated by reference. Preferably the maximum energy rate is selected at a level slightly below that at which shrinkage of the tissue is prevented. Perameters of the rate at which tissue is heated are previously described herein.

Referring to FIGS. 2–6, the curvature of surfaces 54–56 are selected to engage the inner walls of organ 24. Expansion assembly 12 is preferably used to seal transected organ segments 24a and 24b. To seal the transected organ, edges 64 and 66 of the incision or lesion of organ segments 24a and 24b are placed in tight proximity to form a seam 68 using conventional means. Next, the expansion assembly 12, in a contracted position as shown in FIG. 3, having the cylindrical section 52 positioned fully forward on portions 44, 46 and 48 is fed through a slit 70 (FIG. 1) on organ 24 adjacent to the seam 68. Once the expansion assembly is in proper position, the distal ends of media 28a–28c are aligned on the seam 68 (FIG. 4), and cylindrical section 52 is moved rearward along tapered portions 44–48. This rearward movement forces portions 18, 20 and 22 to expand radially outward away from axis 12 resulting in surfaces 54, 55 and 56 engaging the inner walls of organs segments 24a and 24b. This engagement holds edges 64 and 66 in alignment along the seam 67 while organ 24 is being heated.

Referring to FIG. 1, energy source 16 is then activated and optical energy is delivered through media 28a–28c to seam 68 to form a denatured proteinaceous substance that seals the edges 64 and 66 together. The amount of optical energy provided and the duration of the optical energy is dependent on the tissue type as previously discussed. Referring to FIG. 4, optical energy may be delivered to the inner walls of organ 24 simultaneously through media 28a, 28b and 28c. Alternately, the optical energy may be delivered through each of media 28a and 28c in a sequential manner, i.e. first through media 28a, then media 28b and then media 28c.

Referring to FIGS. 1–4, the distal ends of media 28a–28c are placed in assembly 12. The distal ends are rotated about axis 19 (See "I" in FIGS. 2 and 4) at predetermined intervals typically between 0 degrees and 120 degrees, along the inner surface of transmissive material 35 by rotating handles 37, 39 and 41 respectively. Handles 37, 39 and 41 being rotated, rotates deflectors 32a, 32b and 32c, respectively, and subsequently, media 28a, 28b or 28c is rotated to change the area or spot location where optical energy is delivered on seam 68. By rotating media 28a–28c, assembly 12 and portions 18–22 do not have to be moved or rotated to seal another tissue area along seam 68.

After sealing seam 68, cylindrical section 52 is moved forward to its initial position on tapered portions 44–48 (see FIG. 3). The movement of section 52 compressed tubular portions 18, 20 and 22 and closes gap 50. Once a seam has been completely sealed, portions 18–22 on assembly 12 are retracted and then removed from organ 24 through slits 70. It may be preferable that additional portions or additional optical media be placed in assembly 12 to direct energy at slit 70 to seal it after assembly 12 is removed. Depending on the application, the assembly 12 may contain a mechanism mounted on portions 18–22 for providing visual feedback for precise positioning of assembly 12 so that the optical energy is in alignment with the area being treated.

Referring to FIGS. 7, 8A and 9, there is shown an alternate embodiment of an apparatus 110 for tissue welding using assembly 112 that is fed optical energy through media 128a and 128b from an optical energy source 116. Apparatus 110 has a handle assembly 121 which controls the end position of assembly 112. Media 128a and 128b are encased in elongated tubes 130a and 130b, respectively, which are rotated with handles 130 and 140 on assembly 121. Rotating handles 130 and 140 rotate the distal end of media 128a and 128b about an axis 119 extending longitudinally therethrough in the manner previously described to change the position of the distal end of media 128a and 128b.

Assembly 112 includes elongated tubular portion 118 and end tubular portion 120. Tubular portion 118 is connected to and encloses a cylindrical portion 122 that is preferably constructed of a transmissive material 133. The thickness of material 133 is dependent on the organ type and is selected in the manner previously discussed to maintain the proper distance between the distal end of the media and the organ inner surface. End tubular portion 120 slidably attaches and at least partially encloses cylindrical portion 122. Tubular portions 118 and 120 have oppositely facing edges 124 and 126, respectively, which encircle cylindrical portion 122. A cylindrical portion 122 contains a tab 131 which slides along a slot 135 in portion 120. Slot 135 and tab 131 prevent portion from rotating about portion 122.

During operation, apparatus 110 is placed in a lumen of tubular organ 132 adjacent edges 134 and 136. Edges 134 and 136 of a lesion or transection on organ 132 is placed between edges 124 and 126 and in contact with cylindrical portion 122 using conventional devices. Tubular portion 120 is connected to a distal end of rod 129 that is turned by and anchored at rod's 129 proximate end with handle 130. The distal end of rod 129 has a threaded portion 138 that extends into a slot 139 in the center of portion 120. In response to handle 130 being turned, threaded portion 138 moves into and out of slot 139 as shown in FIG. 8A and FIG. 8B. Referring to FIG. 8B, the movement of threaded portion 138 forces portion 120 to slide along portion 122 to move edge 124 toward and away from edge 126. Handle 130 is turned until edges 134 and 136 engage and hold the organ edges 134 and 136 in tight approximation.

Once edges 134 and 136 are in tight approximation, optical energy is applied from the source 116 via media 128a and 128b and through material 133 to the organ 132. Optical energy is delivered with sufficient power and duration to heat substantially all of the tissue edges to the predetermined non-destructive temperature as previously described. When an area of the tissue edges is heated, the optical energy from the source is disabled, and handles 140 and 142 are rotated to change the angular position of the distal ends of media 128a and 128b on the inner surface of portion 122 about rod 129. This change in positions permits apparatus 110 to heat another area between the tissue edges 134 and 136 in the manner described previously in connection with FIG. 4. The distal of media 128a and 128b continue to be rotated until the entire transection or lesion is sealed. After sealing edges 134 and 136 of organ 132, handle 130 is turned to disengage organ 132 from edges 124 and 126. Once disengaged assembly 112 is removed from the lumen of organ 132.

Referring to FIGS. 10, 11 and 12, there is shown another alternate embodiment of an apparatus 10 designated generally as apparatus 210 for tissue welding having assembly 212 connected with media 228a–228c to an energy source (not shown). Assembly 212 has a proximate assembly 216 and a distal assembly 316. Proximate assembly 216 includes a portion 218, a portion 220 and a portion 222, which engage and disengage with the inner walls of luminal tissue or organ 232.

Distal assembly 316 includes a portion 318, a portion 320 and a portion 322, which engage and disengage with the inner walls of luminal tissue or organ 232. Portions 218–222, and 318–322 engage and disengage the inner walls of organ 232 in response to handgrip 326 on assembly 221 being turned clockwise and counterclockwise by the user.

Assembly 212 includes tubular portion 218–222 and tubular portions 318–322 which enclose a three section cylindrical portions 225a–225c constructed of the previously described transmissive material. Each of the sections of cylindrical portions 225a–225c is adhesively connected to a respective one of portions 218–222. Tubular portions 218–222 and 318–322 have oppositely facing edges 224–228 and 324–328 respectively which encircle cylindrical portions 225a–225c.

Optical energy from an energy source 216 such as the one shown in FIGS. 1 or 7, is fed through conduit using optical media 229a–229c, such as a fiber optic cable, having a proximate end distal end. The proximate end of media 229a–229c is optically connected to the energy source 216. Media 229a–229a extends through rotatable tubes 230a–230c, respectively in flexible throat portion 242. The distal end of fiber optic media 229a–229c exits tubes 230a–230c, respectively, and terminates in assembly 212 on an inner wall of portions 225a–225c. Optical energy exits the distal end of fiber optic media 229a–229c and is directed through portions 225a–225c, respectfully, at the inner walls of organ 232. Deflectors 233a–233c are mounted on the distal end of tubes 230a–230c, respectively, to rotate the distal ends of media 229a–229c within assembly 212 about axis 219 extending longitudinally through assembly 112 to heat another area on the tissue without changing the orientation of tubular assembly 212 in organ 232.

An energy source 216 feeds optical or other thermal energy through fiber optical media 229a–229c. The rate of the energy feed is dependent on the thickness of tissue of the walls of organ 232 to be reconstructed as discussed previously.

Portions 218–222 and 318–322 are connected to cylindrical throat portion 242 and 342 respectively through tapered portions 244–248 and 344–348, respectively. Portions 218–222 are separated from each other by gap 250, and engage each other along one end of the gap 250. Portions 318–322 are separated from each other by gap 350, and engage each other along one end of gap 350. An elongated cylindrical section 252 encircles throat portion 242, while cylindrical section 352 encircles throat portion 342. A hollow outer rod 260 is connected at a proximate end to handgrip 226 and at a distal end to throat portion 242. Rod 260 has a head 262 rotatably anchored in a slot 364 in and cylindrical section 352. Outer rod 260 has forward milled threads 361 which connected to portion 363 that extend inward toward forward axis 219 in portion 342. Rod 260 has reverse milled threads 261 connected to section 254 of section 252 that extend through a slot 244 of portion 242 in handle 221. Rod 260 rotates about axis 219 with handgrip 242 to force section 254 to move forward (or backward depending on the direction of handle rotation) resulting in section 252 sliding along tapered portion 244–248. Simultaneously to section 252 sliding, section 363 moves forward and backward along section 352 resulting in section 352 sliding along portions 344–348.

Referring to FIG. 11, portions 261 and 361 are threaded such that when handle 262 moves clockwise, sections 252 move in the direction of arrow A, and sections 252 and 352 move in the opposite direction when handle 242 is rotated counterclockwise. Due to the elastic properties of the materials in which portions 218–222 and 318–322 are constructed, tubular portions 218–222, and 318–322 expand away from each other in an outwardly radially manner when sections 252 and 352 slide along tapered portions 244–248 and 344–348, respectively, in the directions of arrows A and B.

Tubular portion 218–222 and 318–322 expand radially inward when sections 252 and 352 move in the directions of arrows A and B respectively. By expanding portions 218–222 and portions 318–322, expansion assembly 212 contacts the inner walls of organ 232. By using a rod 260 to control the expansion and contraction, portions 218–222 and 318–322 expand and contract at the same rate.

Referring to FIGS. 11 and 12, an inner rod 270 is fed through outer rod 260 and distal hollow outer rod 267.

Rod 270 has a ring 271 that is anchored in a slot 272 on the inner surface of rod 260. Inner rod 270 has threads that mate with the threads on the inner surface of distal rod 267 adjacent throat portion 347. Bars 282 and 284 extend across rods 260 and 267. Bars 282 and 284 are mounted to rod 260 with eyelets 290 and 292, and are mounted to rod 267 with eyelets 294 and 296. Bar 282 has heads 296 and 297 on its ends and bar 284 also has heads 298 and 299 on its ends. Heads 296-299 prevent bars 282 and 284 from sliding out of the eyelets.

Handle 328 is connected to rod 270. When handle 328 is rotated clockwise and handle 242 is kept stationary, rod 270 moves along threads 274 on rod 267, thereby forcing rods 270 along with section 352 and portions 318-322 to move in the direction of arrow C toward portions 218-222. When handle 328 is rotated counterclockwise and handle 242 is kept stationary, portions 318-322 are forced to move opposite to the direction of arrow C. When portions 318-322 move in the direction of arrow C, rods 260 and 267 slide along bars 282 and 284. When portions 318-322 move toward portions 218-222 (the direction of arrow C), edges 224-228 and 324-328 move toward each other to seal tissue in the manner discussed in connection with FIGS. 7-9. A tab/slot configuration may formed with portions 225a-225c and portion's 318-322 inner surface to prevent portion 318-322 from rotating when rod 270 rotates in rod 267.

During operation of apparatus 210, assembly 212 is positioned in the lumen of organ 232 adjacent the edges of the area to be sealed. The assembly 212 is expanded, tissue of organ 232 is placed between edges 224-228 and 324-328 abutting portions 225a-225c using conventional means. Edges 324-328 are moved in the direction of arrow C by the method previously discussed to clamp the edges of the incision or lesion in place. Energy from the source 216 is fed through media 229a-229c at the edges of the clamped lesion or incision. Energy is applied at an area on the tissue edges with a sufficient rate to raise the temperature in the tissue at the edges of the lesion to a predetermined non-destructive temperature range as previously discussed.

Once the area is heated the distal ends of media 229a-229c are moved as previously described to heat another tissue area and heat the entire circumference of the incision/lesion. After sealing the lesion/incision, edges 324-328 are moved in a direction opposite to arrow C to release the tissue edges. Assembly 212 is then contracted and removed form organ 232.

This concludes the description of the preferred embodiments. A reading by those skilled in the art will bring to mind various changes without departing from the spirit and scope of the invention. It is intended, however, that the invention only be limited by the following appended claims.

What is claimed is:

1. An apparatus for sealing an incision or lesion having edges on a luminal tissue, the apparatus comprising:
  a first and second generally cylindrical outer portions each having an oppositely facing side edge, said cylindrical outer portions enclosing a generally tubular inner portion having an outer wall;
  means for sliding at least one of said cylindrical outer portions on said tubular inner portion to move one of said side edges toward the other of said side edges such that when said side edges are drawn toward each other said side edges urge the edges of the incision or lesion together in tight approximation and against the outer wall of said tubular inner portion;
  a source of energy sufficient to heat tissue to form a denatured proteinaceous substance;
  means for delivering energy from the source through said tubular inner portions at the tightly approximated edges of the tissue, said delivering means operative to apply energy to heat an area on the tightly approximated tissue within a nondestructive range bounded by a minimum temperature at which tissue forms a denatured proteinaceous substance and a maximum temperature at which water in the tissue would boil.

2. The apparatus as recited in claim 1 further comprising means for rotating the delivering means within said tubular assembly to heat another area on the edges of the tightly approximated tissue within the nondestructive range without changing the orientation of the cylindrical outer portions in the luminal tissue.

3. The apparatus as recited in claim 1 wherein said first cylindrical outer portion has a first outer portion and second outer portion, said first outer portion being operative to expand radially away from the second outer portion to engage the inner wall of the luminal tissue.

4. The apparatus as recited in claim 2 wherein said source of energy is optical energy, and wherein said delivering means includes at least one fiber optical cable that has a proximate end connected to said energy source and a distal end disposed adjacent said inner surface of at least one of said portions.

5. The apparatus as recited in claim 4 wherein said inner portion has an axis extending longitudinally therethrough and wherein said rotating means includes a tube with a deflector that engages with the cable to change the angular position of said cable distal end about the axis.

6. The apparatus as recited in claim 1 wherein said cylindrical outer portions have at least three radial portions which expand radially outward away from an axis extending longitudinally through the center of said tubular assembly.

7. The apparatus as recited in claim 1 wherein said inner portion is constructed from a material transmissive to energy from said source that heats tissue to the nondestructive range.

8. The apparatus as recited in claim 6 further comprising means for permitting the radial portions to expand away from each other and for contracting the radial portions toward each other.

9. A method for sealing edges of lesions or incisions on luminal tissue, the method comprising the steps of:
  aligning oppositely facing side edges of a first and second generally cylindrical outer portion;
  enclosing with the first and second generally cylindrical outer portion a generally tubular inner portion having an outer wall;
  placing the first and second generally cylindrical outer portion and the enclosed inner portion into the luminal tissue;
  placing edges of the incision or lesion between the oppositely facing side edges;
  sliding at least one of said cylindrical outer portions on said tubular inner portion to draw one of said side edges toward the other of said side edges;
  urging the edges of the incision or lesion together in tight approximation and against the outer wall of said tubular inner portion when the side edges are drawn toward each other;

providing a source of energy sufficient to heat tissue to form a denatured proteinaceous substance;

delivering energy from the source with a delivery means which directs energy through said tubular inner portion at the tightly approximated edges of the tissue; and applying energy to heat an area on the tightly approximated tissue within a nondestructive range bounded by a minimum temperature at which tissue forms a denatured proteinaceous substance and a maximum temperature at which water in the tissue would boil.

10. The method as recited in claim 9 further comprising the step of rotating the energy means within said tubular assembly to heat another area on the tightly approximated tissue within the nondestructive range without changing the orientation of the cylindrical outer portions in the luminal tissue.

11. The method as recited in claim 9 further comprising the steps of forming a first outer portion and second outer portion on said first cylindrical outer portion; and radially expanding said first outer portion away from the second outer portion to engage the inner wall of the luminal tissue.

* * * * *